(12) United States Patent
Schubert

(10) Patent No.: US 10,987,166 B2
(45) Date of Patent: Apr. 27, 2021

(54) SYSTEM FOR SURGICAL TREATMENT

(71) Applicant: IMS GmbH, Tutzing (DE)

(72) Inventor: Michael Schubert, Tutzing (DE)

(73) Assignee: IMS GmbH, Tutzing (DE)

( * ) Notice: Subject to any disclaimer, the term of this patent is extended or adjusted under 35 U.S.C. 154(b) by 0 days.

(21) Appl. No.: 16/337,317

(22) PCT Filed: Sep. 29, 2017

(86) PCT No.: PCT/EP2017/074783
§ 371 (c)(1),
(2) Date: Mar. 27, 2019

(87) PCT Pub. No.: WO2018/060429
PCT Pub. Date: Apr. 5, 2018

(65) Prior Publication Data
US 2019/0336217 A1  Nov. 7, 2019

(30) Foreign Application Priority Data

Sep. 30, 2016 (DE) ................. 10 2016 118 663.5

(51) Int. Cl.
*A61B 18/22* (2006.01)
*A61N 5/06* (2006.01)
(Continued)

(52) U.S. Cl.
CPC ............ *A61B 18/22* (2013.01); *A61N 5/0603* (2013.01); *A61B 2018/00577* (2013.01);
(Continued)

(58) Field of Classification Search
CPC .................................................. A61B 18/22
See application file for complete search history.

(56) References Cited

U.S. PATENT DOCUMENTS 5,748,657 A * 5/1998 Gaddis ................ A61B 18/20
372/38.02
5,787,107 A   7/1998 Leger et al.
(Continued)

FOREIGN PATENT DOCUMENTS

DE   10 2008 044 977      * 7/2010
DE   10 2008 044 977 A1    7/2010
(Continued)

OTHER PUBLICATIONS

International Search Report and Written Opinion issued in PCT/EP2017/074783, dated Jan. 4, 2018, respectively, 16 pages (including translation).

*Primary Examiner* — William J Levicky
(74) *Attorney, Agent, or Firm* — Sterne, Kessler, Goldstein & Fox P.L.L.C.

(57) ABSTRACT

A system for surgical treatment, in particular endovenous laser treatment, includes a laser device and an application module, wherein the laser device comprises a laser light source having at least one first laser diode element and the application module is optically connectable or connected to the laser light source. The application module is designed as a flexurally flexible catheter having an optical waveguide which comprises an RFID chip with a parameter and/or release coding, wherein the laser device comprises a controlling means with an RFID transmitter and receiver unit for reading from and writing to the RFID chip. The controlling means is configured such that an activation of the laser light source ensues in response to the RFID receiver unit detecting a predetermined parameter and/or release coding, and a timestamp is stored on the RFID chip for the invalidating of the catheter.

17 Claims, 6 Drawing Sheets

(51) Int. Cl.
   *A61B 18/00*  (2006.01)
   *A61B 18/20*  (2006.01)
   *A61N 5/067*  (2006.01)

(52) U.S. Cl.
   CPC ............ *A61B 2018/00589* (2013.01); *A61B 2018/00702* (2013.01); *A61B 2018/207* (2013.01); *A61B 2018/2272* (2013.01); *A61N 2005/067* (2013.01)

(56) References Cited

U.S. PATENT DOCUMENTS

| | | | | |
|---|---|---|---|---|
| 2004/0167500 | A1* | 8/2004 | Weckwerth | A61B 18/203 606/9 |
| 2006/0247609 | A1* | 11/2006 | Mirkov | A61B 18/203 606/9 |
| 2007/0173811 | A1* | 7/2007 | Couture | A61B 18/1445 606/39 |
| 2008/0033300 | A1* | 2/2008 | Hoang | A61B 18/20 600/474 |
| 2009/0248004 | A1 | 10/2009 | Altshuler et al. | |
| 2009/0248041 | A1* | 10/2009 | Williams | A61B 18/22 606/130 |
| 2013/0304164 | A1* | 11/2013 | Zanata | A61B 18/203 607/89 |
| 2015/0057649 | A1 | 2/2015 | Lewinsky et al. | |
| 2015/0272654 | A1* | 10/2015 | Esch | A61B 18/1492 606/34 |

FOREIGN PATENT DOCUMENTS

| | | |
|---|---|---|
| DE | 20 2005 022 114 U1 | 2/2014 |
| EP | 1 410 766 A1 | 4/2004 |
| EP | 2620119 | 7/2013 |
| WO | WO 2014/126558 A1 | 8/2014 |

* cited by examiner

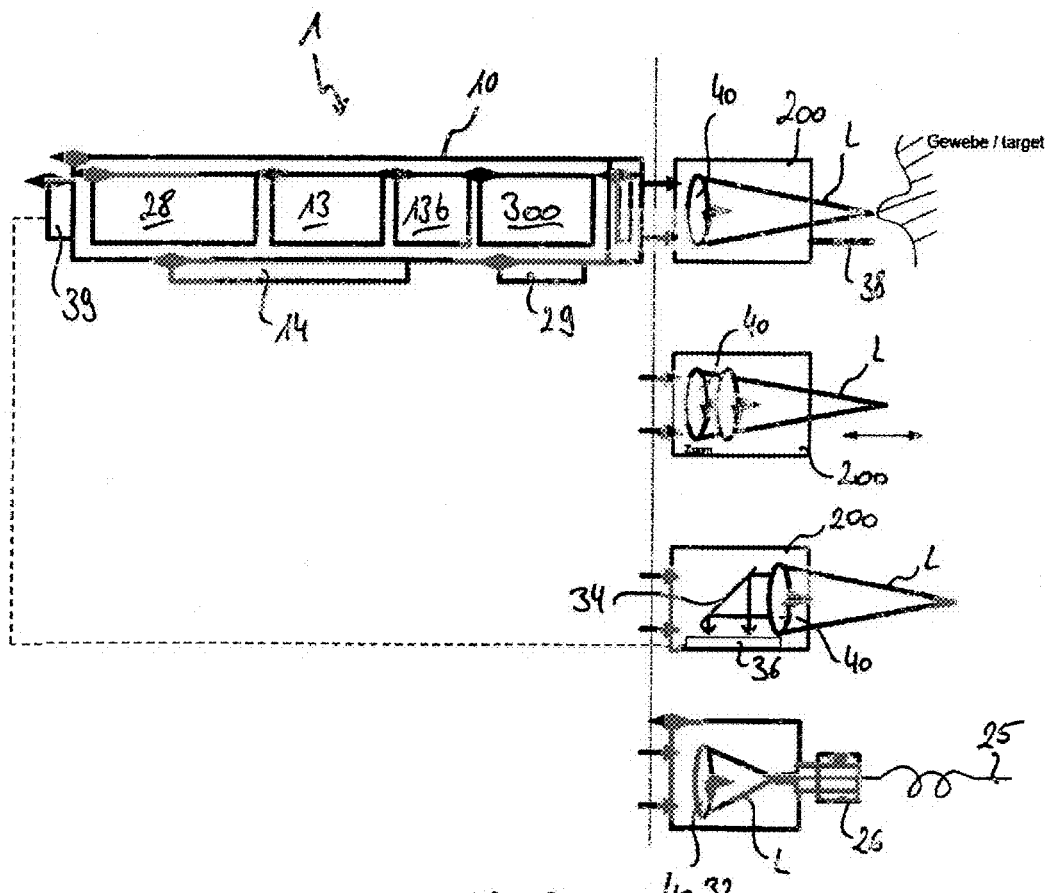
Fig. 8
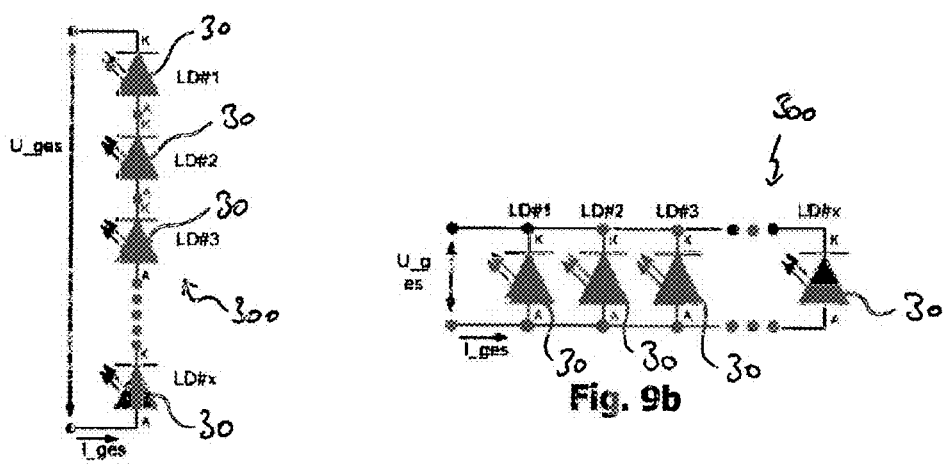
Fig. 9a  Fig. 9b

SYSTEM FOR SURGICAL TREATMENT

BACKGROUND

The invention relates to a system for surgical treatment, in particular endovenous laser treatment, in accordance with the preamble of claim 1. A system of this type is known for example from DE 10 2008 044 977 A1.

The known system comprises a multifunctional laser device having a laser diode capable of emitting a laser light at a wavelength of 1920 nm. An optical fiber is employed to apply the laser light, whereby application is particularly intended for the fields of urology, gastroenterology and otolaryngology.

DE 20 2005 022 114 U1 describes a system for surgical treatment which comprises a light-emitting device having an excitation light source and a wave-length conversion member as well as a catheter or endoscope respectively able to be connected to the light-emitting device. The endoscope comprises an optical waveguide optically coupled to the light-emitting device in order to guide light through the catheter to the treatment site. The light source can have a laser diode element with a nitride semiconductor which em its light in a wavelength range between 350 nm and 500 nm, preferably between 420 nm and 490 nm. Such wavelengths are suitable for illuminating the treatment site yet effect no direct treatment of tissue. For surgical treatment purposes with the known device, a separate instrument is instead guided via the catheter or endoscope respectively to the site of treatment.

A system for the surgical treatment of tissue using laser light is known from US 2009/0248004 A1. The system comprises a laser device and a handpiece which is connectable to the laser device via an optical waveguide. The handpiece can be directed toward an area of tissue such that laser light generated within the laser device can be used to coagulate tissue. The known device makes use of either nitride semiconductor-based LEDs or laser diodes as the laser light source. A wavelength range of 600 nm to 1500 nm is proposed for the treatment of veins. Disadvantageous with the known device is using a wavelength shorter than 1800 nm, which requires a high power density from the laser light source. The emitted laser light thereby penetrates deeper into the tissue structures and can thus undesirably damage the underlying tissue structures. In addition, due to the higher power density requirement of the known device, the overall size of the laser apparatus is also increased, which necessitates stationary treatment. At the same time, the treatment involves an invasive procedure as there needs to be direct access to the veins.

WO 2014/126558 A1 discloses a medical laser system having a laser device and a fiber optic, whereby RFID technology is used to ensure that certain parameters of the device are only activated upon connection of a suitable fiber optic. However, this does not address the problem of the fiber optic being used multiple times on different devices which, particularly in minimally invasive surgical procedures, can lead to the transmission of pathogens and serious consequences for patients.

BRIEF SUMMARY

The task of the invention consists of indicating a system for surgical treatment which is compactly constructed, easy to handle and able to be economically produced as well as safe for patient use.

The invention solves this task by the subject matter of claim 1.

The invention inasmuch proposes a system for surgical treatment, in particular endovenous laser treatment, which comprises a laser device and an application module. The laser device comprises a laser light source having at least one first laser diode element. The application module is optically connectable or connected to the laser light source. The invention in particular provides for the laser diode element to comprise at least one semiconductor layer of an antimonide compound and is thus configured such that laser light can be generated at a first wave-length between 1800 nm and 2000 nm, particularly at a wavelength of 1940 nm. The laser device can be regulated such that continuous or pulsed laser light is or can be generated at the aforementioned wavelengths.

By making use of a semiconductor layer from an antimonide compound, the invention provides a semiconductor diode laser which directly emits laser light in a wavelength range of between 1800 nm and 2000 nm with a high electrical-optical efficiency. A complex pumping mechanism, as for example known from Thulium YAG lasers, can thus be dispensed with. That leads to the laser device of the inventive system being able to be of particularly compact structure.

According to the invention, it is provided for the laser device to be used in conjunction with an application module designed as a catheter. The use of a catheter enables minimally invasive surgical treatment. For example, endovenous therapies can thus be performed easily and less unpleasantly for the patient. Generally speaking, setting a wavelength between 1800 nm and 2000 nm has proven particularly advantageous for laser light treatment by means of any application module. A high surgically therapeutic benefit can be achieved at these wavelengths with low power densities.

The wavelength selected with the invention has in this respect multiple advantages. On the one hand, good treatment of different kinds of tissue of the human body is thereby achieved since the proposed wavelength is well absorbable due to the high water content of the tissue. At the same time, the proposed wavelength achieves enabling largely loss-free light transmission by means of economical glass fiber optics. As a result, lower power is thus required from the laser light source in order to provide the same therapeutic benefit compared to other wavelengths as used to date in the prior art. Particularly compared to the wavelengths proposed with the system according to US 2009/0248004 A1 as cited at the outset, the laser light output which the present invention requires for the same therapeutic success is at least halved.

The proposed wavelength additionally has advantages in terms of treating tissue since the penetration depth of the laser light is limited by the laser light's higher absorption rate in the tissue. The unintentional damaging of deeper layers of tissue which are usually not visible to the user can thus be efficiently prevented. The inventive system is insofar particularly suited to treating thin layers of tissue, for example treating venous walls which generally have a thin wall thickness. As a result, the surgical treatment is thus very gentle on the patient such that the healing process as a whole is accelerated. This is also accompanied by improved laser treatment precision.

Using lower laser light outputs to achieve the desired surgical effect also results in the particular advantage of the laser device of the inventive system being able to be of particularly compact design. Since the laser light source has a low power consumption requirement, air can be used to provide for the cooling of the laser light source. In the context of the invention, it is insofar preferentially provided for the laser device to comprise an air-cooled laser light source. A complex coolant circuit, which generally requires a large amount of space, is thereby eliminated. All told, the external dimensions of the laser device can thus be reduced, which enables mobile applications of the laser device.

The preferential variant of the invention provides for the semiconductor layer of the laser diode element to comprise a gallium antimonide compound or consists of a gallium antimonide compound. It has been shown that such a semiconductor layer, in particular a gallium antimonide semiconductor layer, can be used particularly efficiently in order to directly generate laser light of sufficient power density in order to be used for surgical treatment. It is thereby in particular provided for the laser light source to comprise direct emitting single emitter laser diodes. In particular, a plurality of laser diode elements interconnected into an array can be provided. In order to achieve the highest power density possible, the collimated beams of the single emitter laser diodes can be densely packed, particularly in a hexagonal lens structure. Said hexagonal arrangement represents the greatest packing density for achieving a quasi-rotationally symmetric sum beam shape which is in turn advantageous for maximum coupling efficiency in round application fibers (catheters). The possible use of single emitter laser diodes, for example in the form of broad area laser diodes, effects an improvement in beam quality compared to bar laser diodes.

Generally speaking, a plurality of first laser diode elements which generate laser light at a first wavelength of between 1800 nm and 2200 nm can be provided. It can additionally be provided for the laser light source to comprise at least one second laser diode element which emits laser light at a second wavelength. Multiple second or further (third, fourth, etc.) laser diode elements can also be provided. The second wavelength can be different from the first wavelength.

The at least one second laser diode element is preferably designed as a single emitter laser diode or as a broad area laser diode and can be a component of the same laser diode module comprising the at least one first laser diode element. It is also possible for the second laser diode element to be optically coupled to the laser diode module comprising the first laser diode element.

Combining multiple laser diode elements emitting different wavelengths has the advantage of increasing the inventive system's possible applications. Thus, different applications can be realized with the same laser device. For example, tissue coagulation can be achieved at a first wavelength whereas laser light of a second wavelength is used for cutting tissue (dissection) and/or for coagulation and/or ablation of tissue and/or for illuminating the object of the treatment. Other possible application combinations are possible given the appropriate selection of laser diode elements of different wavelength.

The invention provides for the application module to comprise an optical waveguide. The optical waveguide is flexible. The application module in particular forms a flexurally flexible catheter encompassing the optical waveguide.

It is preferably provided for the laser device and/or the application module to comprise a coupling optic, in particular at least one lens, for coupling the laser light produced by the laser light source into the optical waveguide. Noted in particular is that it is explicitly provided in the context of the invention for the laser light source to comprise a plurality of laser diode elements of different wavelength. It can insofar be provided for all the laser diode elements to be connected to the coupling optic such that laser light of different wavelength can be coupled into the same optical waveguide of the application module. Laser light of different wavelength can in this way be guided to the treatment site via the optical waveguide of the application module. This substantially increases the flexibility of the system since different forms of treatment can be realized without changing the application module, in particular without a catheter change.

Specifically, a hybrid laser light application of different wavelength is possible, for example to enable a larger-volume coagulation on the one hand and, by simply switching the corresponding laser diode elements, a minimally intrusive dissection on the other hand. The invention insofar preferentially provides for the first laser diode element and the second laser diode element to be arranged such that the laser light emitted by the first and the second laser diode element can be alternatingly and/or simultaneously coupled into the, particularly the same, optical waveguide, in particular via the coupling optic.

Integrating the coupling optic into the laser device is particularly advantageous. Doing so thus reduces the complexity of the application modules able to be combined with the laser device. The application modules, preferably catheters, which are often designed as disposable products, can in this way be economically produced.

The laser diode elements can be connected together in electrical series connection. This applies on the one hand to the plurality of first laser diode elements which can be coupled together in series. On the other hand, the plurality of second laser diode elements can also be electrically connected together in series. The electrical interconnecting of the laser diode elements in series reduces the total electrical currents within the laser device. Smaller cable diameters can thus be used which on the one hand saves space and on the other hand enables improved air cooling within the laser device.

The laser device in the inventive system comprises a controlling means connected to the laser light source. The controlling means can be configured such that a pulsed and/or continuous laser light emission can be regulated. Preferably, the controlling means exclusively controls the laser light source electronically. This has the advantage of being able to set any modes of control. In particular, the controlling means can realize different electrical pulse wave modulations. In the case of pulsed excitation, the peak optical output power of the laser diode elements can be superelevated to a significant degree in relation to the nominal continuous power output depending on the duty cycle, typically by a factor of 2 to 4. The laser device can thus also be subsequently adapted to future treatment models.

The inventive system additionally preferentially provides for the laser light source to be operable at an electrical operating DC voltage of no more than 50 volts. Using directly emitting single emitter laser diode elements achieves an overall high energy efficiency. Supplying a relative low DC voltage of 50 volts to the laser light source suffices in this regard. This has significant advantages particularly with regard to medical device standards. On the one hand, the low operating voltage reduces electrical hazard of the medical device. In particular, minimal stray currents are to be expected at low voltages such that operating personnel safety is considerably increased.

The low operating DC voltages as required for the operation of the laser light source also enable mobile operation of the laser device. It is in this regard particularly preferentially provided for the laser device to comprise a voltage supply, in particular an accumulator, which provides the operating DC voltage of no more than 50 volts. Low operating DC voltages can be readily provided by compact direct current voltage sources, for examples batteries or an accumulator. A compact and portable laser device can inasmuch be realized. In this variant, the system according to the invention is thus particularly suitable for mobile use.

The invention further preferentially provides for the laser device to comprise a gas-tight and/or liquid-tight housing, whereby at least the laser light source is arranged in the housing. It can specifically be provided for at least the laser light source, and where appropriate also further components of the laser device, to be hermetically sealed. The gas/liquid-tight housing serves that purpose. Doing so enables the laser device to also be operated in damp and/or dusty environments. Further fields of application inasmuch arise in conjunction with the high mobility provided by the compact laser device. In order to achieve the overall gas-tightness and/or liquid-tightness of the housing or the laser device respectively, it can be additionally provided for a protective glass guard to be provided on a module connection of the laser device. The protective glass guard tightly covers the connection to the application module, which enables light transmission from the laser device to the application module, in particular the optical waveguide of the catheter. The protective glass guard is preferably arranged and/or fixed to the module connection of the laser device so as to be replaceable without opening the housing of the laser device.

With respect to the application module, in particular the optical waveguide disposed within the application module, it is intended for a coupling with the laser device to only be possible when the optical waveguide is suitable for the emitted wavelength of the laser light source. In order to enable a corresponding identification of the optical waveguide of the application module, the invention provides for the application module, in particular the optical waveguide, to comprise an RFID chip having a parameter and/or release coding. The RFID chip is preferably arranged at a proximal end of the application module, in particular the optical waveguide.

The controlling means of the laser device comprises an RFID transmitter and receiver unit for reading from and/or writing to the RFID chip. The controlling means is thereby configured such that a parameter presetting and/or an activation of the laser light source ensues in response to the RFID receiver unit detecting a predetermined parameter/release coding. In other words, suitable laser device operating modes for the application module are only enabled when an application module is connected to the module connection of the laser device, whereby the RFID chip of the application module has a corresponding coding which the controlling means's RFID transmitter and receiver unit recognizes as parameter and/or release coding. Operating errors are in this way prevented.

In addition, the laser parameters utilized, in particular the total laser energy applied or the number of times the respective application module was used, can be written back to the RFID chip during treatment. It is specifically provided for the controlling means to generate a timestamp which is stored on the RFID chip and documents the first use of the application module. Doing so enables disposable application modules to be rendered invalid or respectively unusable after use.

As already described in detail, the laser device in the system according to the invention is characterized by a particularly compact design based particularly on the use of a laser light source having directly emitting antimonide semiconductor layer laser diode elements. It is insofar preferential for the laser device to exhibit a volume not exceeding 10 $dm^3$, in particular no more than 9.5 $dm^3$. It can be specifically provided for the laser device to exhibit a height not exceeding 150 mm, a width not exceeding 250 mm and/or a depth not exceeding 250 mm. The laser device is preferably configured in such a way that the mass of the laser device amounts at most to 10 kg, preferably at most 8 kg. The small external dimensions and low weight of the laser device contribute significantly to the laser device's properties which enable mobile use of the system as a whole.

The inventive system can additionally provide for the laser device to comprise an auxiliary laser light source and a photosensor. The auxiliary laser light source and the photosensor can be coupled to the controlling means such that a laser light intensity of the laser light source can be adjusted as a function of a specific fluorescent light signature of the tissue to be treated. The aim of this laser device design is the influencing of the laser light intensity of the laser light source by means of a control, wherein the fluorescent light signature of the tissue to be treated is taken as the control input variable.

It was recognized that optical tissue properties such as fluorescence and reflection change during surgical treatment of the tissue, particularly during coagulation. There is thus a direct correlation between the tissue's fluorescent light signature and degree of coagulation. In this preferential variant, the invention provides for an auxiliary laser light source directing laser light to the tissue to be treated which is reflected and radiated back to the optical waveguide of the application module. Thus, reflected auxiliary laser light reaches the photosensor by way of the optical waveguide of the application module. The auxiliary laser light exhibits a fluorescent light signature which is dependent on the coagulation degree of the treated tissue. The controlling means then evaluates the fluorescent light signature registered by the photosensor and accordingly adapts the laser light intensity of the laser light source to the treated tissue's degree of coagulation. A closed control loop is insofar formed. In particular, unintentional damaging of tissue which is not to be treated can be efficiently prevented by the reducing or disabling of the laser device output depending on the control signal.

A further preferential embodiment of the invention provides for the laser device to comprise a temperature sensor for detecting a temperature of the tissue to be treated. The temperature sensor can be coupled to the controlling means such that a laser light intensity of the laser light source can be adjusted as a function of the tissue temperature. The temperature sensor can be realized as an optical sensor. Inasmuch, the previously described photosensor can also be used to measure the temperature of the treated tissue. It is alternatively possible to provide for a separate temperature sensor which is for example brought into direct content with the tissue to be treated.

In general, the invention preferentially provides for the controlling means to comprise an evaluation unit which is coupled to the photosensor and/or the temperature sensor and measures the temperature of the tissue or respectively the degree of coagulation of the tissue on the basis of the detected fluorescent light signature and the detected parameters. The evaluation unit preferably incorporates the auxiliary laser light source. The auxiliary laser light source can thereby emit a pulsed laser beam or a continuous laser beam.

The evaluation unit can moreover have amplifier functions in order to amplify the reflected auxiliary laser light for evaluation purposes.

In one preferential embodiment, the inventive system can additionally comprise a storage unit for storing treatment information. In particular, information on the laser light output, the amount of energy applied and/or the period of operation and/or type of optical waveguide, etc. can be stored in the storage unit. The data saved or to be stored can be output via an electronic interface, particularly wirelessly. This allows statistics and treatment documentation to be easily generated, thereby facilitating documentation of the treatment.

To be noted in general is that the laser device can be connected to different application modules. A set or module kit respectively can inasmuch be provided, whereby the laser device can be combined with different application modules as the base module. The application modules enable different forms of treatment and differ from one another in particular by their optical properties.

One preferential embodiment of the invention provides for the laser device to be of such a compact and lightweight construction that it can be controlled with one hand like a pen. In particular, the laser device can essentially have the size and form of a pen so that it can in particular be easily and consistently used as a laser scalpel. The laser device preferably has an accumulator integrated into this pen-like configuration so that it can be operated with energy self-sufficiency.

BRIEF DESCRIPTION OF THE DRAWINGS

The following will draw on exemplary embodiments referencing the accompanying schematic drawings in describing the invention in greater detail. Shown are:

FIG. 8 a longitudinal sectional view through an inventive system according to a preferential embodiment, wherein the laser device is structured like a pen and combinable with different application modules; and FIG. 9a, 9b respective circuit arrangements of multiple laser diodes.

DETAILED DESCRIPTION

Figure 1:
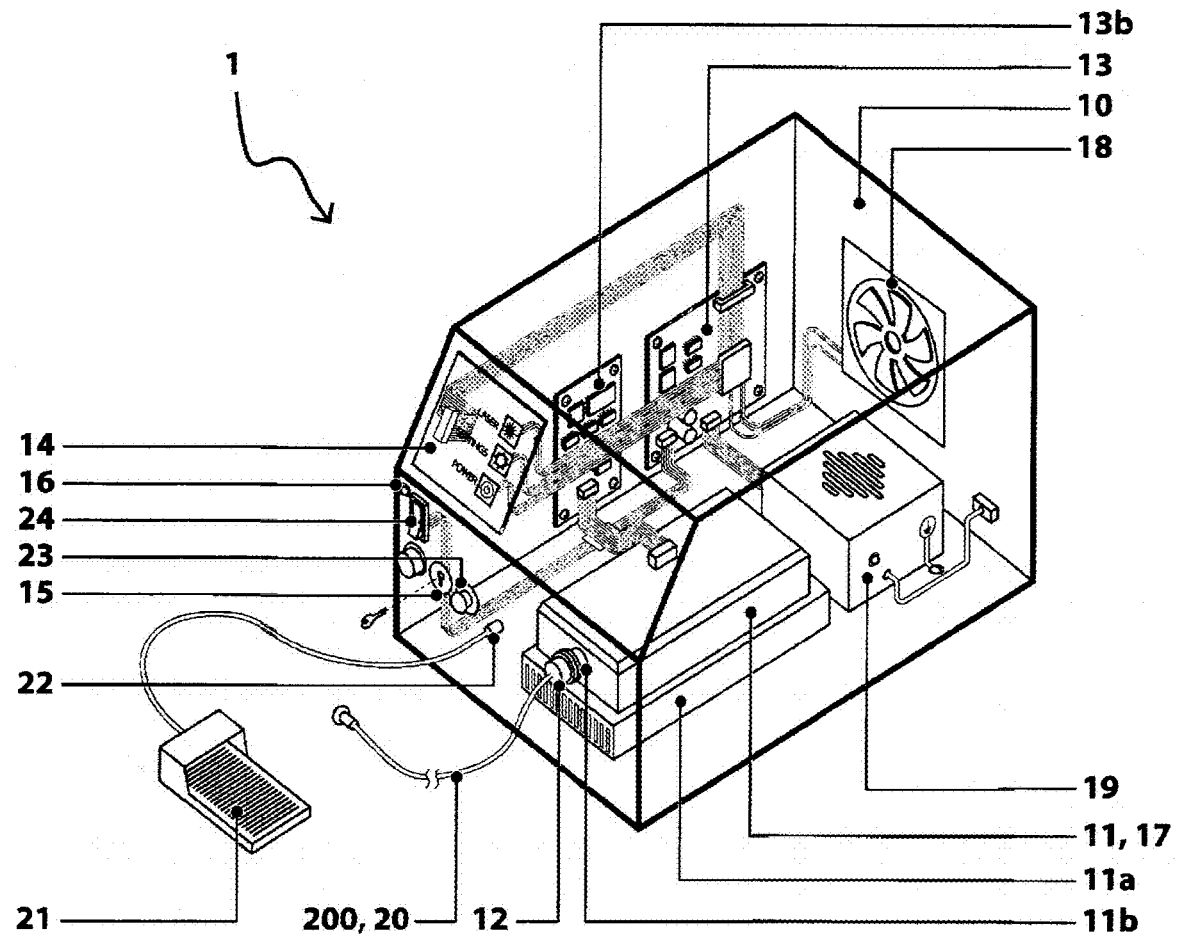
FIG. 1 a perspective, partially transparent representation of a laser device for an inventive system according to a preferential embodiment.

As can be seen in FIG. 1, the laser device 1 comprises an external housing 10 which encloses the individual components of the laser device 1. A laser light source 11 having a cooling element 11a and a coupling optic 11b is arranged inside the housing. The coupling optic 11b leads to a module connection 12 formed in the housing. The module connection 12 enables the laser device to be connected to an application module 200, in particular a catheter 20, whereby only a proximal end piece of the catheter 20 is depicted in the attached figure for reasons of clarity.

The catheter 20 essentially comprises an optical waveguide 25 which is encased in a protective sheathing. The optical waveguide 25 is optically connectable to the coupling optic 11b via the module connection 12 such that laser light produced by the laser light source 11 can be efficiently coupled into the optical waveguide of the catheter 20.

The laser device 1 further comprises a controlling means 13 which is connected to the laser light source 11. The controlling means 13 can be further connected to a (not shown) storage unit so that treatment parameters can be continuously stored. The controlling means 13 is moreover coupled to control elements, in particular a touchscreen 14. Switches connected to the controlling means 13 can be further provided in order to, for example, activate the emission of laser light. Illustrated for example in the depicted embodiment is a key switch 15 which can be connected to the controlling means 13. A luminous display 16 can additionally be seen in the drawing which indicates the current operating mode of the laser device 1. The luminous display 16 can be formed for example by a lamp with a bulb or an LED.

Additionally recognizable in FIG. 1 is that the laser device 1 comprises an emergency stop switch 23 in addition to the key switch 15. The emergency stop switch 23 has the usual form of a mushroom head switch. A main switch 24 connected to the controlling means 13 is furthermore arranged on the external housing 10. A foot switch 21 for activating the laser light source 11 is further provided which is connectable to a foot switch connection 22 of the laser device 1.

As can be seen in the drawing, the laser light source 11 is arranged in a housing, in particular an interior housing 17. The interior housing 17 is hermetically sealed and directly connected to the cooling element 11a. Specifically, the interior housing 17 is of gas-tight and/or liquid-tight design. It is just as preferentially provided for the coupling optic 11b to be arranged in a hermetically sealed housing. In particular, the interior housing 17 can also extend over the coupling optic 11b, whereby it is not precluded for the interior housing 17 to be of multi-part construction.

The controlling means 13 is likewise arranged in a housing, wherein it is preferentially provided for the housing to at least be liquid-tight.

A fan unit 18 is further arranged in a rear wall of the external housing 10. The fan unit 18 serves to circulate air within the laser device 1, in particular within the external housing 10. This thereby ensures that sufficient air flows around the fins of the cooling element so as to achieve an efficient cooling of the laser light source 11.

A power supply unit 19 is further arranged within the external housing 10. The power supply unit 19 is provided between the laser light source 11 and the fan unit 18 in the depicted embodiment. A different arrangement of the power supply unit 19 is possible. In particular, an external power supply unit 19 can be utilized. The power supply unit 19 is coupled to the controlling means 13 and serves as a DC voltage source for the controlling means 13 and the laser light source 11.

The laser light source 11 preferably comprises a plurality of laser diode elements, in particular multiple gallium antimonide semiconductor laser diode elements. Individual laser diode elements can thereby emit different wavelengths. It can in any case be recognized that interconnecting multiple single emitting semiconductor laser diode elements achieves overall system scalability. In particular, differing numbers of laser diode elements can be interconnected into an array depending on application such that laser devices of different output intensities can be easily produced.

The exemplary embodiment of a laser device for a system according to the invention as depicted in FIG. 1 is preferably configured so that the laser light source 11 emits laser light in a wavelength range of from 1800 nm to 2200 nm, preferably at a wavelength of 1940 nm. This wavelength is particularly suitable for endovenous laser treatment. It can thereby be provided for the laser device 1 to be configured such that the laser light source 11 provides a laser light output of no more than 10 watts of laser light output at a distal end of an optical wave-guide 25 of the catheter 20. It is preferably provided for the laser light at the distal end of the optical waveguide to have an output of approximately 7 watts.

Figure 2:
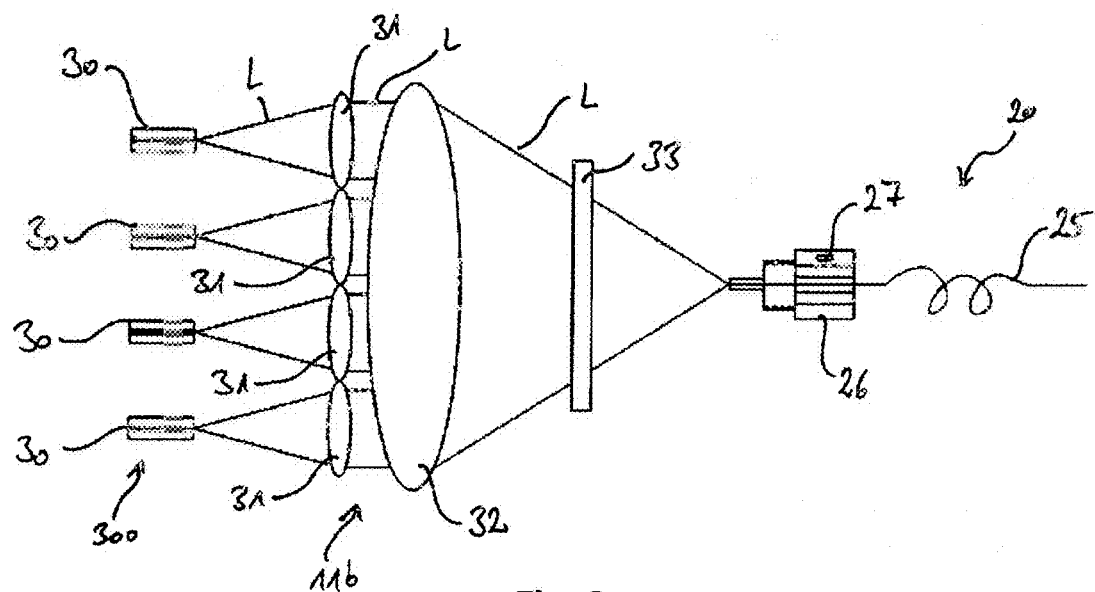
FIG. 2 a schematic depiction of a laser diode array having a coupling optic for coupling laser light into an application module for an inventive system according to a preferential embodiment.

The structure of an array comprising multiple laser diode elements 30 is shown schematically in FIG. 2. The laser diode elements 30 are preferably designed as single emitter diodes. The laser diode elements 30 can in particular be designed as broadband laser diodes. The laser diode elements 30 emit laser light L which is in each case bundled via a collimating lens 31. Each laser diode element 30 is thereby allocated a collimating lens 31. The bundled laser light then reaches a coupling lens 32. The coupling lens 32 receives the bundled laser light of all the laser diode elements 30 and couples the entire volume of laser light into optical waveguide 25. To that end, the optical waveguide 25 has an optical fiber connector 26 on a proximal end which is connectable to the module connection 12 of the laser device 1.

The laser device 1 comprises, preferably in the external housing 10, a protective glass guard 33. The protective glass guard 33 protects the coupling optic 11b, formed by the collimating lenses 31 and the coupling lens 32, from contamination or other impurities.

Additionally recognizable in FIG. 2 is that the optical waveguide 25, which is generally a component of an application module 200, is provided with a RFID chip 27 on optical fiber connector 26. The RFID chip 27 communicates with the controlling means 13 of the laser device 1 during operation. The RFID chip 27 can in particular comprise data on parameters of the application module 200 employed, in particular the optical waveguide 25. The RFID chip 27 is additionally writeable so that data can be stored on the RFID chip 27 by way of the controlling means 13. Timestamp data can specifically be stored so that after a predetermined number of applications, the application module 200, in particular the optical waveguide 25, will no longer be enabled for operation with the laser device 1.

In other words, it can be provided for the controlling means to run a comparison between the RFID chip of the catheter 20 and an internal database. As soon as the RFID receiver unit detects a specific RFID parameter and/or release coding of the catheter 20, the controlling means 13 enables the laser light source, wherein it is also provided for the controlling means 13 to enable different modes of the laser light source depending on the release coding detected. Thus, the laser device 1 can be used for example both in veterinary medicine as well as in human medicine, wherein when coupling a catheter 20 for veterinary medicine, different setting options are provided for the laser light emission than when coupling a catheter 20 for human medicine. Operating errors can thus be efficiently prevented. The catheter 20 can generally encompass a disposable catheter or a reusable catheter 20.

Figure 3:
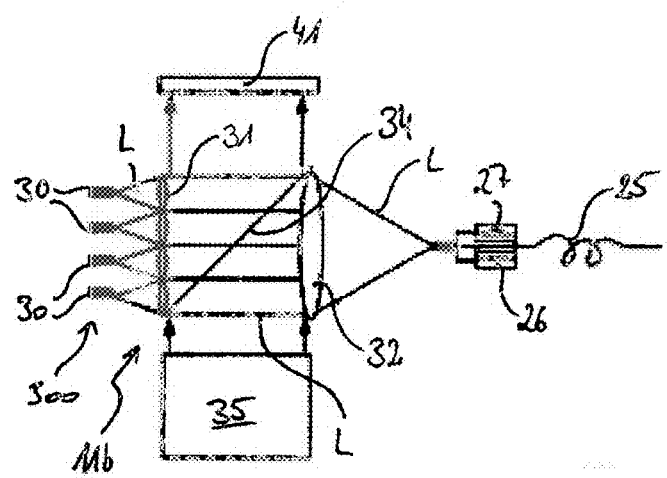
FIG. 3 a schematic depiction of a laser diode array having a coupling optic for coupling laser light into an application module for an inventive system according to a further embodiment.

FIG. 3 shows another configuration of the coupling optic 11b of an inventive system according to a preferential embodiment. The FIG. 3 structure of the coupling optic 11b is substantially similar to the FIG. 2 structure. Multiple laser diode elements 30 are inasmuch likewise provided, each being allocated a collimating lens 31. The collimating lens 13 bundles the laser light L of each laser diode element 30. The bundled laser light L reaches a coupling lens 32 which couples the laser light L into the fiber 25a of an optical waveguide 25. The optical waveguide 25 has a corresponding optical fiber connector 26 with an RFID chip 27 at its proximal end.

In contrast to the embodiment according to FIG. 2, an auxiliary laser light source 35 is additionally provided in the embodiment according to FIG. 3 which is arranged laterally to the path of the bundled laser light L beam. The auxiliary laser light source 35 emits auxiliary laser light which is used in identifying the tissue structure of the tissue to be treated. A beam splitter 34 is arranged to that end in the beam path between the collimating lenses 31 and the coupling lens 32. The beam splitter 34 deflects the auxiliary laser light coming from the auxiliary laser light source 35 so that the auxiliary laser light is likewise coupled into the fiber 25a of the optical waveguide 25. An auxiliary laser light detector 41 is assigned to the auxiliary laser light source 35 which detects the auxiliary laser light and which is signal-connected to the controlling means 13 for transmitting data on the auxiliary laser light.

Figure 4B:
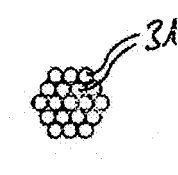
FIG. 4a, 4b a respective cross-sectional view in each case of an optical wave-guide of an application module of an inventive system according to a preferential embodiment.
Figure 4A:
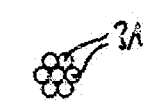

In order to achieve the most optimal possible coupling and utilization of the laser light L emitted by the laser diode elements 30, it is advantageous for the collimating lenses 31 to be packed in an arrangement as tightly as possible to each other. FIGS. 4a and 4b for example show a hexagonal packing of the collimating lenses 31, whereby seven collimating lenses 31 are provided in the FIG. 4a example embodiment and 19 collimating lenses are provided in the FIG. 4b example embodiment. The same number of laser diode elements 30 and collimating lenses 31 are in each case preferably provided in the laser device 1.

With respect to the configuration of the optical waveguide 25, FIGS. 5a to 5e show a number of variants which are regarded as being particularly preferential in the context of the present invention. Applicable to all the optical waveguides 25 is that they comprise a fiber 25a encompassing a distal fiber end 25b. The laser light exits the optical waveguide 25 via the distal fiber end 25b. The distal fiber end 25b can thereby essentially form a vertical plane to the longitudinal axis of the fiber 25a as is shown by way of the example in FIG. 5a.

Figure 5A:
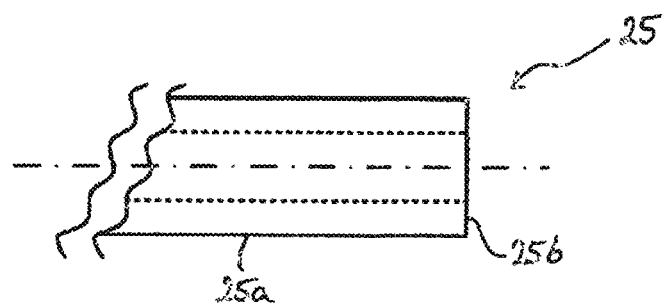
FIG. 5a-5e a respective longitudinal sectional view in each case through a collimating lens array for a coupling optic for coupling laser light into an application module of an inventive system according to a preferential embodiment.
Figure 5B:
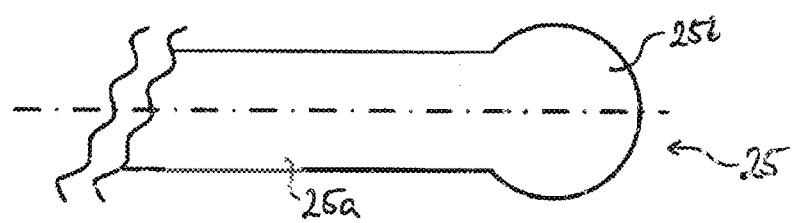

FIG. 5b shows a particularly preferential configuration of the distal fiber end 25b. The distal fiber end 25b here exhibits a ball-shaped or spherical design. Such a design is insofar preferential as it can prevent injury to tissue. In addition, the design of the distal fiber end 25b according to FIG. 5b is advantageous because the enlarged cross-sectional diameter in the region of the distal fiber end 25b relative to the fiber 25a achieves an easier feed of the optical waveguide 25 through the catheter. In particular, the friction between the optical waveguide 25 and the inner wall of the catheter is reduced.

Figure 5C:
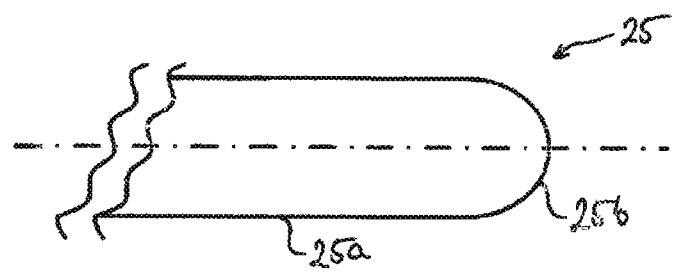

FIG. 5c shows an example of a further atraumatic end, wherein the distal fiber end 25b is only curved without exhibiting a mean bulging as shown in the FIG. 5b example.

Figure 5D:
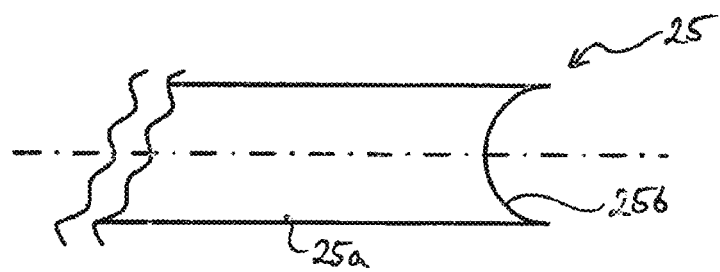
Figure 5E:
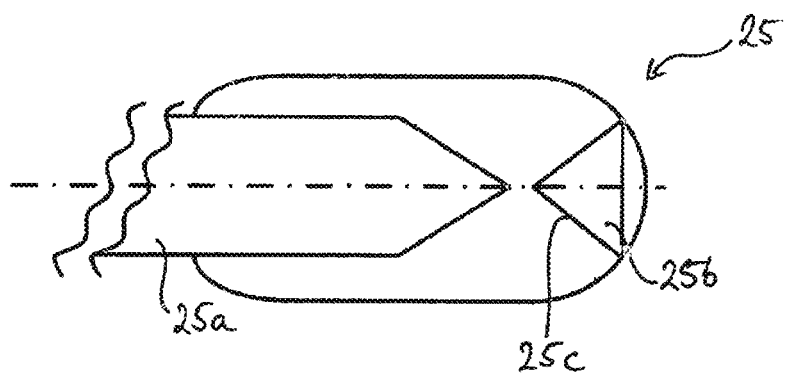

For particularly concentrated beam conduction, a concave distal fiber end 25b can also be provided as shown in FIG. 5d. Lastly, it may be advantageous in some applications to emit the laser light L radially. The optical waveguide 25 according to FIG. 5e shows a distal fiber end 25b configuration with a reflector 25c which ensures that the laser light L directed through the fiber 25a exits the optical waveguide 25 as radial emittance.

Figure 6:
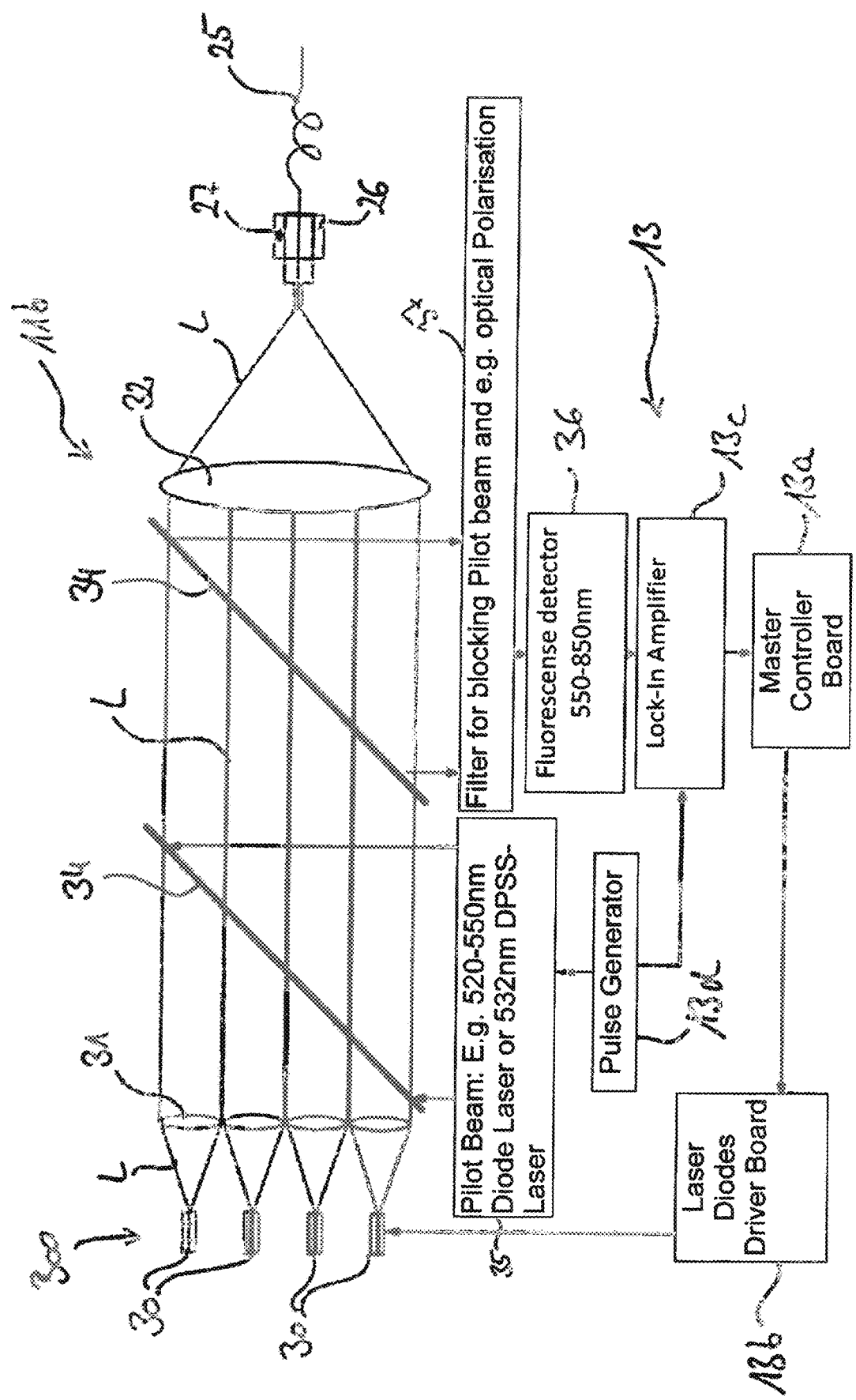
FIG. 6 a schematic depiction of a controlling means of a laser diode array having a coupling optic for coupling laser light into an application module for an inventive system according to a preferential embodiment.

FIG. 6 in turn shows a coupling optic 11b which ensures that light from the laser diode elements 30 efficiently couples into the optical waveguide 25. The coupling optic 11b according to FIG. 6 insofar differs from the coupling optic 11b according to FIG. 3 by the providing of two beam splitters 34a, 34b. The beam splitters 34a, 34b are arranged serially one behind the other along the path of the laser light. The further structuring to the coupling optic 11b corresponds to the structure as per FIGS. 2 and 3. Specifically, a plurality of laser diode elements 30 are provided, each associated with a collimating lens 31. The two beam splitters 34 are disposed between the array of multiple collimating lenses 31, which are preferably arranged hexagonally, and a coupling lens 32. An optical fiber connector 26, provided at a proximal end of an optical waveguide 25, follows the coupling lens 32 in the direction of the optical path of the laser light L. The coupling lens 32 couples the laser light L into the optical waveguide 25, in particular its fiber 25a. The optical fiber connector 26 can incorporate an RFID chip 27.

FIG. 6 shows in detail the controlling of the laser light source 11 and an auxiliary laser light source 35. The control thereby comprises a master controller 13a to that end which is electrically coupled to a laser diode driver 13b. The laser diode driver 13b acts on the laser diode elements 30 and provides for the appropriate electrical control of the laser diode elements 30. The master controller 13a furthermore receives data of an amplifier 13c which is in turn coupled to a pulse generator 13d and a fluorescent light detector 36. The pulse generator 13d is assigned to an auxiliary laser light source 35 which conducts auxiliary laser light into the optical path of the laser light L via a first beam splitter 34a. The first beam splitter 34a is preferably configured so as to be barely penetrable by the auxiliary laser light but instead reflective. In particular, the first beam splitter 34a can be designed to be highly reflective to a wavelength range from 520 nm to 550 nm. The second beam splitter 34b on the other hand is designed to be highly reflective to a wavelength as can be expected for feedback fluorescent light. In particular, the second beam splitter 34b can be designed to be highly reflective to a wavelength range of from 550 nm to 850 nm. Both beam splitters 34a, 34b are preferably highly transmissive to a wavelength range of from 1800 nm to 2.200 nm, particularly 1940 nm, so that the treatment laser light can essentially pass through without hindrance.

The fluorescent light detector 36 is arranged downstream of an optical filter 37. Fluorescent light, which is fed back into the laser device 1 via optical waveguide 25, reaches the second beam splitter 34b and is deflected by the second beam splitter 34b and directed to the fluorescent light detector 36 via optical filter 37. The parameters, in particular the wavelength, of the fluorescent light can subsequently be evaluated in the controlling means 13 and can then be used to appropriately control the laser diode driver 13b and/or the pulse generator 13d.

The laser device 1 described herein preferably operates at a wavelength in the range of from 1800 Nm to 2000 Nm, particularly preferentially at a wavelength of 1940 nm. Laser diode elements 30 having a semiconductor with at least one semiconductor layer comprising antimonide are preferably used thereto. In particular, the semiconductor layer can comprise a gallium antimonide compound.

Figure 7:
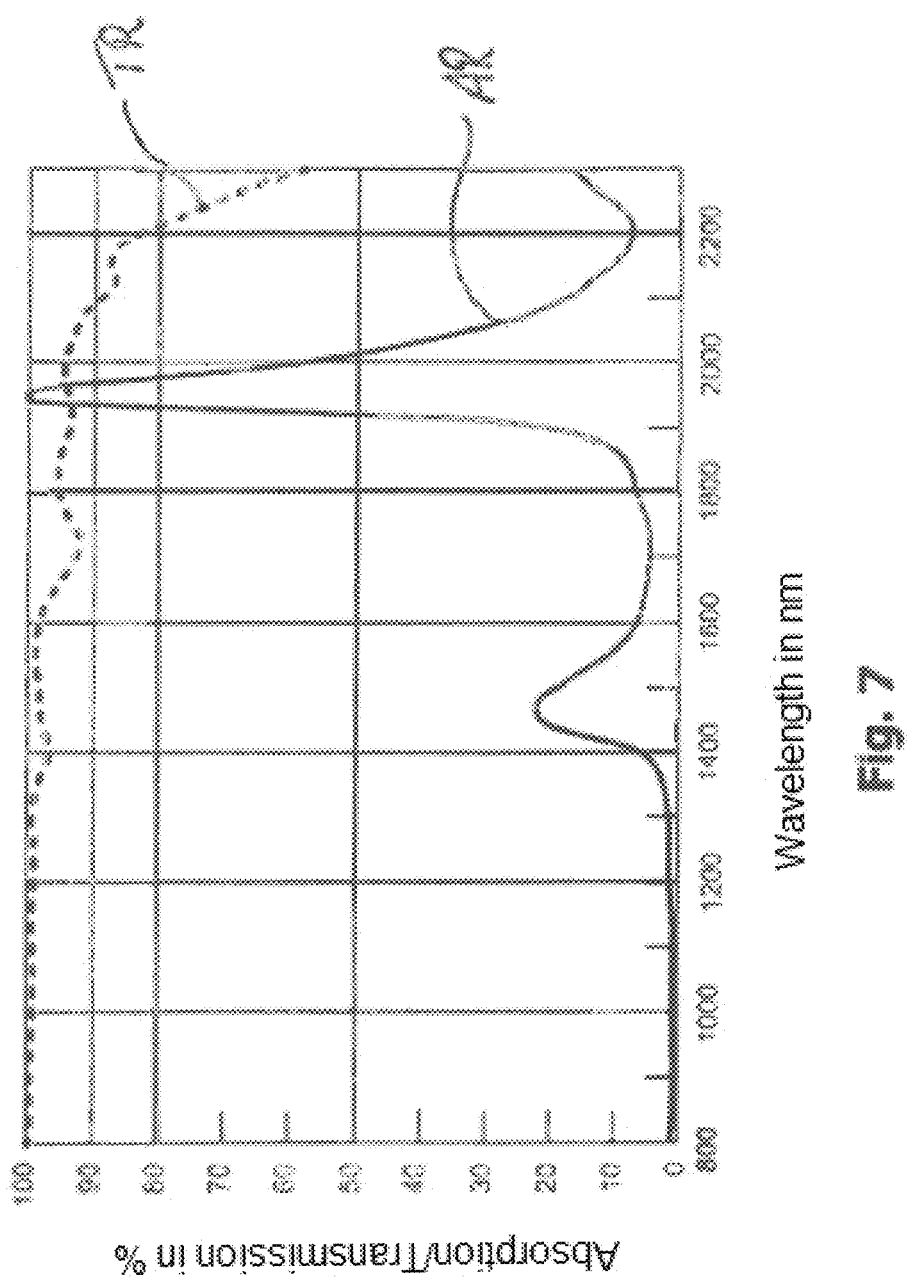
FIG. 7 a diagram representing the wavelength-dependent absorption rate of laser light in human tissue.

FIG. 7 clearly shows why the preferential wavelength range herein for the treating of tissue is particularly advantageous. Wavelength in nanometers is plotted along the X-axis in the diagram according to FIG. 7. The absorption rate AR of human tissue and the transmission rate TR of an optical fiber are depicted along the Y-axis. The respective values are thereby percentually scaled along the Y-axis.

The diagram of FIG. 7 clearly indicates that the absorption rate of human tissue rises considerably in the range between 1800 and 2200 nm. That means that laser light at such a wavelength has particularly good effect in the treatment of human tissue. At the same time, the transmission rate TR of an optical fiber is barely impacted within this wavelength range so that overall low power is required in order to achieve high effect in the tissue. Only at wavelengths above 2200 nm does the transmission rate TR drop off sharply. It is clearly apparent from this that the laser device 1 described herein has high efficiency at comparatively low power consumption.

The electrical output or respectively power consumption of the laser device 1 is generally related to the current the laser diode elements 30 receive. It is particularly preferential to use laser diode elements 30 designed as single emitter laser diodes. Such single emitter laser diodes can be connected in series one after another, whereby the total current required for the operation of an array of multiple laser diode elements 30 is relatively low. This relationship is quite visible in FIGS. 9a and 9b. It can be seen that a lower total current I_ges is required in the series connection according to FIG. 9a than in the parallel connection of multiple laser diode elements 30 according to FIG. 9b.

A particularly preferential example embodiment of the inventive system is shown in FIG. 8. The laser device 1 is of pen-like design in this example embodiment and preferably dimensioned such that a user can operate it with one hand. The laser device 1 thus essentially resembles a pen, whereby the laser device 1 is correspondingly compact and thus enables easy and extremely mobile use. The pen, or laser device 1 respectively, comprises an external housing 10, wherein an accumulator 28 or battery respectively is integrated into the external housing 10. The accumulator 28 is electrically connected to the controlling means 13 which can preferably be designed as a microcontroller on a printed circuit board (PCB). The controlling means 13 further incorporates a laser diode driver 13b or is coupled to a laser diode driver 13b respectively. The laser diode driver 13b is in turn connected electrically to a laser diode module which can comprise a plurality of laser diode elements 30 as well as the coupling optic 11b.

The laser device 1, or the pen respectively, furthermore incorporates an activation switch 29 via which the laser diode elements 30 can be switched on or off. Lastly, it is preferentially provided for the laser device 1, or pen respectively, to comprise a display and control elements. Preferably, the display and control elements are combined as a touchscreen 14. The laser device 1 further comprises an interface, for example a USB port 39. The USB port 39 can be used on the one hand for exchanging data and on the other for connecting the accumulator 28 to a power source for the purpose of recharging said accumulator 28. With respect to data exchange, it can in particular be provided for the USB port 39 to be signal-connectable to a fluorescent light detector 36 in order to enable control of the laser diode elements 30 on the basis of data relative to the tissue to be treated. Such a fluorescent light detector 36 can for example be integrated into one of the application modules 200 as shown as an example in FIG. 8. In this context, the dotted line symbolizes a feedback channel from a fluorescent light detector 36 to USB port 39.

The laser device 1 additionally comprises a protective glass guard 33 arranged in the path of the laser beam, preferably after the coupling lens. The protective glass guard 33 can preferably be screwed onto the external housing 10 of the laser device 1. This facilitates the easy replacing or changing of the protective glass guard 33.

A plurality of different application modules 200 can furthermore be attached or respectively screwed onto the protective glass guard 33 or the laser device 1 respectively. FIG. 8 depicts an example of four different application modules 200. An application module 200 with a respective output optic 40 in each case can thus be provided. The output optic 40 can comprise one or more lenses which focus the laser beam L.

It is provided in a first variant of an application module 200 according to FIG. 8 for the application module 200 to additionally comprise a spacer 38 which serves to ensure even spacing between the tissue to be treated and the application module 200. This is particularly advantageous when the output optic 40 has a fixed focal distance/focal length. It can be alternatively provided for the application module to have a variable focal distance/focal length. FIG. 8 likewise depicts such an alternative, whereby the double arrow symbolizes the shift in focal distance/focal length.

Lastly, a beam splitter 34 and a fluorescent light detector 36 can also be integrated into the application module 200 so that fluorescent light fed back into the application module 200 can be detected and sent back to the laser device 1 for the controlling of the laser diode elements 30.

The output optic 40 can additionally be formed by a coupling lens 32 so that the output optic 40 of the application module 200 can couple the laser light into an optical waveguide 25. The application module 200 is to that end preferably connectable to an optical waveguide 25, wherein the optical waveguide 25 preferably comprises a corresponding connecting piece, in particular an optical fiber connector 26, at its distal end.

The system described in the present application is not only suitable for endoscopic surgery, in particular endovenous laser treatment, but has preferential application potentiality, in particular as a so-called laser scalpel, for the dermatology field, e.g. in the removing of fibromas or warts, as well as the fields of gastroenterology, vascular surgery, gynecology, otorhinolaryngology surgery, laparoscopy, orthopedics, pediatrics, pulmonology, urology and/or thoracic surgery. Further application possibilities arise in dentistry and veterinary medicine.

The system described herein can in particular be of modular construction, whereby the laser device 1 constitutes the base module of the modular system. The laser device 1 can however be coupled to different application modules which differ in particular in their structure. Application modules having at least one respective optical waveguide can particularly differ by differing configuring of the optical waveguide, in particular with regard to the distal ends of the optical waveguide.

The following exemplary embodiments are additionally disclosed within the scope of the present application:

1. A system for surgical treatment, in particular for endovenous laser treatment, comprising a laser device 1 and an application module 200, wherein the laser device 1 comprises a laser light source 11 having at least one laser diode element and the application module 200 is optically connectable or connected to the laser light source 11,
   wherein the first laser diode element comprises at least one semiconductor layer from an antimonide compound and is configured such that laser light can be generated at a first wavelength between 1800 nm and 2200 nm, particularly 1940 nm.
2. The system according to exemplary embodiment 1, characterized in that
   the semiconductor layer comprises or consists of a gallium antimonide compound.
3. The system according to exemplary embodiment 1 or 2, wherein the laser light source 11 comprises at least one second laser diode element which emits laser light at a second wavelength differing from the first wavelength.
4. The system according to one of the preceding exemplary embodiments,
   wherein the application module 200 comprises an optical waveguide.
5. The system according to exemplary embodiment 4, wherein the laser device 1 and/or the application module 200 comprises a coupling optic 11*b*, in particular at least one lens, for coupling the laser light produced by the laser light source 11 into the optical waveguide.
6. The system according to exemplary embodiment 5, wherein the first laser diode element and the second laser diode element are arranged such that laser light emitted from the first and second laser diode element can be alternatingly and/or concurrently coupled into the, in particular the same, optical waveguide, particularly via the coupling optic.
7. The system according to exemplary embodiment 5 or 6, wherein a plurality of first laser diode elements and/or a plurality of second laser diode elements are connected together in electrical series connection.
8. The system according to one of the preceding exemplary embodiments,
   wherein the laser device 1 comprises a controlling means 13 which is connected to the laser light source 11 and configured such that a pulsed and/or continuous laser light emission can be regulated.
9. The system according to one of the preceding exemplary embodiments,
   wherein the laser light source 11 is operable at an electrical operating DC voltage of not more than 50 volts.
10. The system according to one of the preceding exemplary embodiments,
    wherein the laser device 1 comprises a voltage source, in particular an accumulator, which provides the electrical operating DC voltage of not more than 50 volts.
11. The system according to one of the preceding exemplary embodiments,
    wherein the laser light source 11 comprises a gas-tight and/or liquid-tight housing 17.
12. The system according to one of the preceding exemplary embodiments,
    wherein the application module 200, in particular the optical waveguide, comprises an RFID chip having parameter and/or release coding and the controlling means 13 comprises an RFID receiver unit for reading the RFID chip, wherein the controlling means 13 is configured such that activation of the laser light source 11 ensues in response to the RFID receiver unit detecting a predetermined parameter/release coding.

13. The system according to one of the preceding exemplary embodiments,
wherein the laser device 1 has a volume not exceeding 10 dm³, in particular no more than 9.5 dm³.
14. The system according to one of the preceding exemplary embodiments,
wherein the laser device 1 comprises an auxiliary laser light source and a photosensor, wherein the auxiliary laser light source and photosensor are coupled to the controlling means 13 such that a laser light intensity of the laser light source 11 can be adjusted as a function of a specific fluorescent light signature of the tissue to be treated.
15. The system according to one of the preceding exemplary embodiments,
wherein the laser device 1 comprises a temperature sensor for detecting a temperature of the tissue to be treated, same being coupled to the controlling means 13 such that a laser light intensity of the laser light source 11 can be adjusted as a function of the tissue temperature.
16. The system according to one of the preceding exemplary embodiments,
wherein the laser device 1 comprises a storage unit for storing treatment information, in particular information on the laser light output, the amount of energy applied and/or the period of operation.
17. The system according to one of the preceding exemplary embodiments,
wherein the laser device 1 can be connected to different application modules (200).
18. The system according to one of the preceding exemplary embodiments,
wherein the laser device (1) is of such compact and lightweight construction that the laser device (1) can be controlled with one hand like a pen.

LIST OF REFERENCE NUMERALS

1 laser device
10 external housing
11 laser light source
11a cooling element
11b coupling optic
12 module connection
13 controlling means
13a master controller
13b laser diode driver
13c amplifier
13d pulse generator
14 touchscreen
15 key switch
16 luminous display
17 interior housing
18 fan unit
19 power supply unit
20 catheter
21 foot switch
22 foot switch connection
23 emergency stop switch
24 main switch
25 optical waveguide
25a fiber
25b distal fiber end
25c reflector
26 optical fiber connector
27 RFID chip
28 accumulator
29 activation switch
30 laser diode element
31 collimating lens
32 coupling lens
33 protective glass guard
34 beam splitter
34a first beam splitter
34b second beam splitter
35 auxiliary laser light source
36 fluorescent light detector
37 optical filter
38 spacer
39 USB port
40 output optic
41 auxiliary laser light detector
200 application module
300 laser diode module
L laser light
AR absorption rate
TR transmission rate

The invention claimed is:

1. A system for surgical treatment, comprising:
a laser device and an application module, wherein the laser device comprises a laser light source having at least one first laser diode element and the application module is optically connectable or connected to the laser light source, wherein the first laser diode element comprises at least one semiconductor layer from an antimonide compound and is configured such that laser light can be generated at a first wavelength between 1800 nm and 2000 nm,
wherein the application module is designed as a flexurally flexible catheter having an optical waveguide configured to route laser light through the catheter and comprising an RFID chip with a parameter and/or release coding, and
wherein the laser device comprises a controlling means with an RFID transmitter and receiver unit for reading from and writing to the RFID chip,
wherein the controlling means is configured to activate the laser light source in response to the RFID transmitter and receiver unit detecting a predetermined parameter and/or release coding from the RFID chip that corresponds to a parameter and/or release coding associated with the laser device, and
wherein a timestamp recording a number of uses of the catheter is stored on the RFID chip by the controlling means for the invalidating of the catheter by the controlling means after a predetermined number of uses of the catheter is recorded by the timestamp.

2. The system according to claim 1, wherein the semiconductor layer comprises or consists of a gallium antimonide compound.

3. The system according to claim 1, further comprising a plurality of first laser diode elements that are connected into an array having a hexagonal lens structure.

4. The system according to claim 1, wherein the laser light source comprises at least one second laser diode element which emits laser light at a second wavelength differing from the first wavelength.

5. The system according to claim 4, wherein the first laser diode element and the second laser diode element are arranged such that laser light emitted from the first and second laser diode element can be alternatingly and/or concurrently coupled into the optical waveguide.

6. The system according to claim 5, wherein a plurality of first laser diode elements and/or a plurality of second laser diode elements are connected together in electrical series connection.

7. The system according to claim 1, wherein the laser device and/or the application module comprises a coupling optic for coupling the laser light produced by the laser light source into the optical waveguide.

8. The system according to claim 1, wherein the controlling means is connected to the laser light source and configured such that a pulsed and/or continuous laser light emission can be regulated.

9. The system according to claim 1, wherein the laser light source is operable at an electrical operating DC voltage of not more than 50 volts.

10. The system according to claim 1, wherein the laser device comprises a voltage source which provides an electrical operating DC voltage of no more than 50 volts.

11. The system according to claim 1, wherein the laser light source comprises a gas-tight and/or liquid-tight interior housing.

12. The system according to claim 1, wherein the laser device comprises an auxiliary laser light source and a photosensor, wherein the auxiliary laser light source and photosensor are coupled to the controlling means such that a laser light intensity of the laser light source is adjusted as a function of a specific fluorescent light signature of the tissue to be treated that is detected by the photosensor.

13. The system according to claim 1, wherein the laser device comprises a temperature sensor for detecting a temperature of the tissue to be treated, the same being coupled to the controlling means such that a laser light intensity of the laser light source can be adjusted as a function of the tissue temperature.

14. The system according to claim 1, wherein the laser device has a volume of no more than 10 $dm^3$.

15. The system according to claim 1, wherein the laser device comprises a storage unit for storing treatment information.

16. The system according to claim 1, wherein the laser device is configured to be connected to different application modules, wherein the different application modules enable different types of treatment.

17. The system according to claim 1, wherein the laser device is configured to be held in one hand like a pen.

* * * * *